(12) United States Patent
Waller et al.

(10) Patent No.: US 6,436,117 B1
(45) Date of Patent: Aug. 20, 2002

(54) SURGICAL INSTRUMENT WITH A CONTINUOUS HOLLOW CHANNEL FOR A FURTHER INSTRUMENT

(75) Inventors: Peter Waller, Gauting; Ulrich Matern, Bollschweil, both of (DE)

(73) Assignee: Karl Storz GmbH & Co. KG (DE)

( * ) Notice: Subject to any disclaimer, the term of this patent is extended or adjusted under 35 U.S.C. 154(b) by 17 days.

(21) Appl. No.: 09/670,727

(22) Filed: Sep. 27, 2000

Related U.S. Application Data

(63) Continuation of application No. PCT/EP99/02080, filed on Mar. 26, 1999.

(30) Foreign Application Priority Data

Mar. 27, 1998 (DE) .......................................... 198 13 781

(51) Int. Cl.[7] ................................................ A61B 17/32
(52) U.S. Cl. ........................ 606/171; 606/207; 606/167; 606/205
(58) Field of Search ........................ 606/205, 206–211, 606/157, 158, 142, 150, 151, 167, 170, 174, 171, 191, 194, 198, 108, 57; 30/165, 191–193, 245, 250, 251; 81/348–349

(56) References Cited

U.S. PATENT DOCUMENTS

| 4,427,014 A | | 1/1984 | Bel et al. ................. 128/751 |
| 4,770,174 A | | 9/1988 | Luckman et al. ........... 128/318 |
| 4,909,789 A | | 3/1990 | Taguchi et al. ............. 604/107 |
| 5,403,326 A | | 4/1995 | Harrison ..................... 606/139 |
| 5,425,705 A | * | 6/1995 | Evard et al. ................ 606/205 |
| 5,454,365 A | * | 10/1995 | Bonutti ...................... 606/198 |
| 5,536,251 A | * | 7/1996 | Evard et al. ................ 606/205 |
| 5,569,299 A | | 10/1996 | Dill et al. ................... 606/205 |
| 5,855,590 A | * | 1/1999 | Malecki et al. ............. 606/205 |

FOREIGN PATENT DOCUMENTS

| DE | 31 46 426 A1 | 11/1981 |
| DE | 33 37 016 T1 | 9/1983 |
| DE | 37 16 764 A1 | 5/1987 |
| DE | 37 09 706 C2 | 10/1987 |
| DE | 91 05 399.4 | 5/1991 |
| DE | 43 07 228 A1 | 3/1993 |
| DE | 196 05 615 A1 | 8/1997 |
| DE | 196 32 298 A1 | 2/1998 |
| DE | 198 13 781 C2 | 10/1999 |
| EP | 0 065 054 | 8/1981 |
| EP | 0 279 358 | 2/1988 |
| FR | 80 07480 | 4/1980 |
| WO | WO95/08946 | 9/1994 |
| WO | WO96/22056 | 1/1996 |

* cited by examiner

*Primary Examiner*—Michael J. Milano
*Assistant Examiner*—Jackie Tan-Uyen T. Ho
(74) *Attorney, Agent, or Firm*—St. Onge Steward Johnston & Reens LLC

(57) ABSTRACT

A surgical instrument is provided having a tubular shaft with working elements arranged at its distal end, at least one of which may be spread apart. The working elements engage through an actuator element with a handle arranged at the proximal end of the shaft for opening and closing the working elements. A continuous hollow channel is provided in the interior of the instrument, into which at least one additional instrument may be inserted. The hollow channel preferably has a cross section corresponding to the inner clearance diameter of the tubular shaft. The working elements are configured such that they do not extend into the cross section of the hollow channel either in opened or in closed condition.

22 Claims, 4 Drawing Sheets

SURGICAL INSTRUMENT WITH A CONTINUOUS HOLLOW CHANNEL FOR A FURTHER INSTRUMENT

CROSSREFERENCE OF PENDING APPLICATION

This application is a continuation of pending international application PCT/EP99/02080 filed Mar. 26, 1999.

BACKGROUND OF THE INVENTION

The invention relates to a surgical instrument having a tubular shaft with working elements arranged at the distal end thereof, at least one of the elements capable of being spread apart. The working elements are connected via an actuator element with a handle arranged at the proximal end of the shaft for opening and closing the working elements. The instrument further comprises a hollow channel passing through the interior of the instrument, into which at least one further instrument may be inserted.

A surgical instrument of the above type is disclosed in the international patent application WO 96 22 056. In an embodiment of the multifunctional surgical instrument disclosed there, the working elements are both formed as spreadable jaw portions. In the closed condition, the jaws substantially close the distal end of the hollow channel, where only a small semi-circular recess is provided at a central portion of each jaw. A small opening results through which a thin cannula of a syringe may pass, after having been inserted from the proximal end into the central hollow channel of the tubular shaft.

In recent times, minimally invasive surgery has become widely Employed and it is common to observe procedures with surgical instruments inside the body with an endoscope. These instruments are introduced into the body by means of a trocar, where relatively small incisions are required initially to introduce the trocar into the body. If a surgical instrument, for example surgical scissors, are introduced at a different location than the endoscope for observing the cutting procedure, then two incisions are necessary.

In these types of operations, one strives to make as few incisions as possible. It is thus known to introduce several instruments into the body through one incision. The shaft or tube of the surgical instrument then is disposed adjacent to the tube of the endoscope. The instruments normally have at least approximately a circular cross section, as does the outer shaft encompassing the two instruments, i.e. the shaft through which the two instruments adjacent to one another are introduced into the body through the single incision. Consequently, only about half of the lumen of the outer shaft is used. Thus with a certain cross sectional dimension of the surgical instrument, the diameter of the outer shaft must be unnecessarily large. Even if a portion of the remaining space can be used as a flushing channel or for other purposes, the available space of the lumen is always insufficiently used.

The object of the present invention is to avoid the above drawbacks and provide a surgical instrument or an instrument system, by which the outer tube diameter remains small even when an additional instrument apart from a surgical instrument is to be passed through the same incision.

SUMMARY OF THE INVENTION

According to the present invention, the hollow channel has a cross section corresponding approximately to the inner clearance diameter of the tubular shaft, and the working elements are configured such that they do not pass into the cross section of an imaginary distal prolongation of the hollow channel in said tubular shaft in either closed or opened condition of said working elements.

The feature has the advantage that the entire interior space of the tubular shaft is available for introduction of a further instrument. At the most, the available cross section is reduced by the usual rod-shaped actuator element, assuming it is passed through the interior of the instrument.

By configuring the working element so as not to enter into the space in opened or closed condition, the full cross sectional area remains available in all operational states or conditions of the working elements. For example it is possible to introduce an endoscope through the continuous hollow channel, with which the manipulations of the working elements can be visually observed. As the working elements do not extend into the continuous hollow space, one can always observe procedures through the centrally introduced endoscope, for example when introducing the instrument with closed jaws. One can also then observe the manipulations of the working elements after having been inserted into the body.

Depending on the given purpose, the working elements can be variously configured, for example for the purpose of grasping and/or cutting, for laying tissue open or the like. Since the entire cross section of the tubular shaft is available as a hollow space, an endoscope with sufficient light intensity and visibility can be employed with relatively small diameter surgical instruments.

The hollow channel can also be employed as a sectioning and/or flushing channel. The combination of a sectioning/flushing channel with an endoscope is also possible, namely when the outer diameter of the endoscope shaft is smaller than the inner diameter of the hollow channel. Fluids or gaseous media can then be supplied or discharged through the intermediate space about the endoscope.

The working elements can also be provided as spreading elements, where other grasping or cutting instruments can then be passed through the hollow channel when the elements are separated.

The construction of the instruments within one another is very slender and as a particular advantage it is emphasized that the functionality of one instrument is not impaired by the other instrument.

In a further embodiment of the present invention, the working elements arranged at the distal end project in one working position as an extension of the wall of the tubular shaft. The advantage in this position is that the surgical instrument takes on the form of a tube in the region of the shaft and the working elements, which can be passed through a trocar for in-sertion into the body, so that a particularly space-saving con-figuration results.

In a further embodiment of the present invention, the working elements themselves have the form of a tube or tube section. The advantage is that the working elements themselves have a large cross section, but do not extend laterally beyond the shaft while allowing a maximal inside free width in the interior of the hollow channel. Thus a maximal inner hollow space is available combined with a slender construction of the surgical instrument and maximal stability of the working elements.

In a further embodiment of the present invention, the at least one actuator element is also formed to be of tubular shape. The advantage is that the actuator element passed through the interior of the instrument represents the least possible impairment in the hollow channel. The actuator element essentially transmits compression or tensile forces, so that the tubular geometry is ideal for transmitting high forces with the thinnest wall thicknesses. The tubular actuator element can also be configured such that it surrounds the hollow space.

In a further embodiment of the present invention, the actuator element comprises recesses acting as guide slots or curves, in which guide pins of the working elements engage. The advantage is that the engagement between the actuator element with the working elements is accomplished with means extending in the circumferential direction or the longitudinal direction of the actuator element, so that the inner hollow channel is not obstructed by these components.

In a further embodiment of the present invention, the actuator element engages the working elements through pivotal intermediate means. The advantage is that extended positions of the pivotal means are possible, which are displaced in the most spacesaving manner, whether when introducing the instrument itself through a trocar or when inserting a further instrument into the inner hollow space.

In a further embodiment of the present invention, the actuator element engages with the working elements through flexible intermediate means. This has the advantage that slender or narrow components are provided which do not enlarge the construction or obstruct the inner hollow channel.

In a further embodiment of the present invention, the working elements are mounted to the shaft by pivot joints. The advantage is that the pivotal mounting on the shaft achieves sufficient stability of the working elements and still saves space.

In a further embodiment of the present invention, the working elements are mounted on the shaft through flexible bands or foil joints. The advantage is that a flat joint construction, narrow in radial direction is possible. Again, sufficient stability is provided and neither the construction width is enlarged nor is the inner hollow channel obstructed.

In a further embodiment, the mounting is provided to have the broadest possible base, preferably approximately the outer diameter of the tubular shaft. This can be achieved for example in that the base is formed as half-rings with two diametrically opposite securement points, on which the working elements or the jaws are arranged.

In a further embodiment of the present invention, the working elements are configured as two jaws of a scissors or a grasping tongs. The advantage is that the surgical instrument is formed as a frequently used instrument with which very strong forces must be transmitted for grasping or cutting procedures. Due to the mentioned configuration, these procedures can be carried out without problem in the slender design while leaving a large portion of the hollow channel free.

In a further embodiment of the present invention, the jaws are formed as tubular sections extending in circumference a little more than 90° and lying adjacent to one another. Their opposing edges are arranged to pass one another in scissor-like manner. This preferred embodiment has the advantage that the jaws neither extend beyond the width of the shaft at its outer periphery, nor is the inner hollow channel impaired. Thus, a maximal inner channel space is available with minimal shaft diameter. The channel completely passes through the shaft so that instruments can be inserted beyond the jaw portion, independent of whether these are opened or closed.

It will be understood that the above-mentioned features and those to be discussed below are not only applicable in the given combinations, but may be present in other combinations or taken alone without departing from the scope of the present invention.

BRIEF DESCRIPTION OF THE DRAWINGS

The invention will be discussed in more detail below in con-junction with selected embodiments.

DETAILED DESCRIPTION OF A PREFERRED EMBODIMENT

Figure 1:
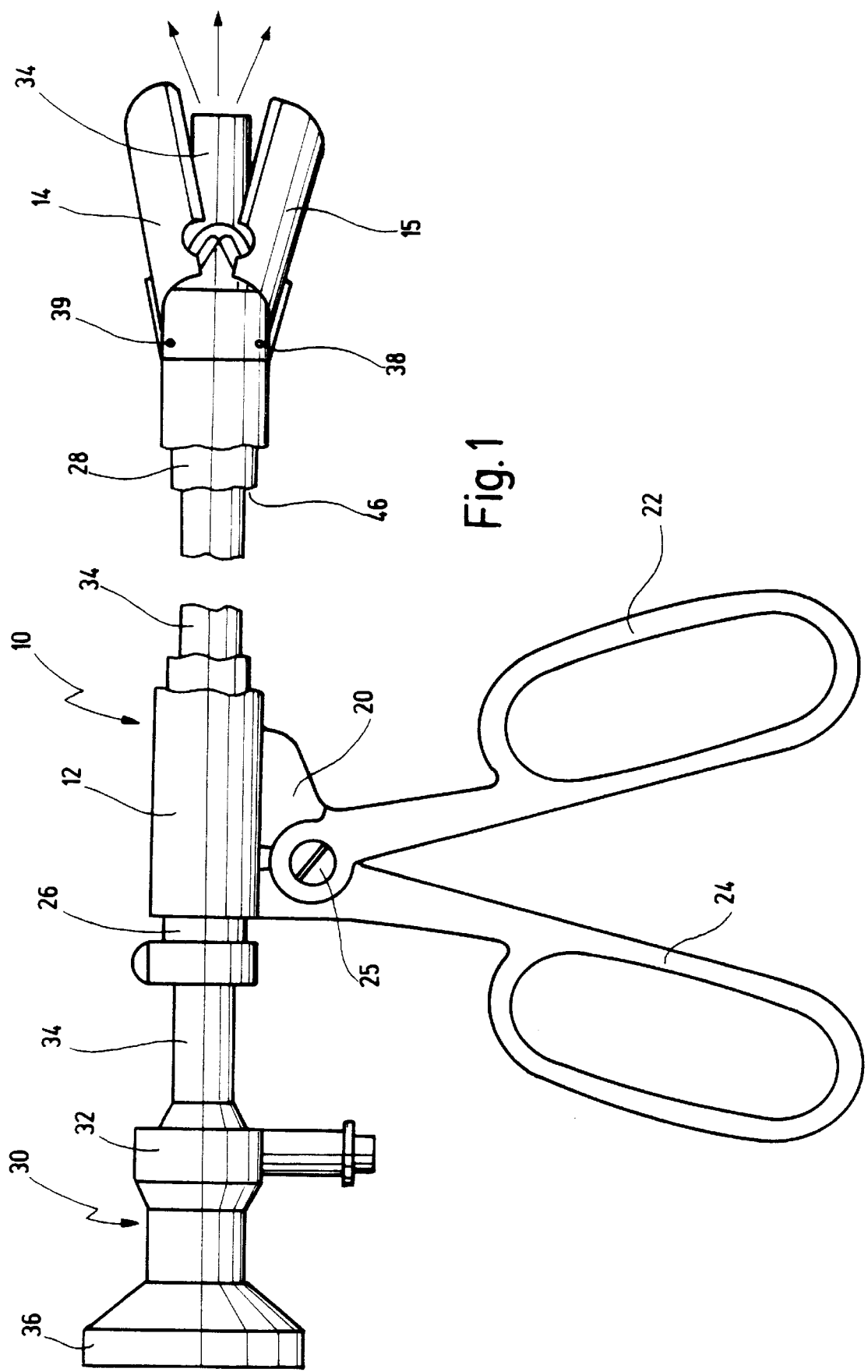
FIG. 1 shows the side view of a surgical instrument of the present invention formed as scissors, where a further instrument, namely an endoscope, is inserted.

A surgical instrument is shown is FIG. 1 and generally designated with the numeral 10. The surgical instrument 10 is a scissors comprising a centrally located elongated tubular shaft 12. Two working elements 14, 15 are pivotally connected to the distal end of the shaft 12 which are configured as jaws 16, 17 to be discussed in more detail below.

A handle 20 is arranged on the proximal end of the shaft 12, which comprises two gripping portions 22, 24 connected to one another by a hinge 25.

The gripping portion 24 is fixedly secured to the outer side of the proximal end of the shaft 12, while the gripping portion 22 is moveable. The moveable portion 22 is connected to an actuator element 26 extending through the interior of shaft 12, which has the form of a tube 28. The outer diameter of the tube 28 corresponds to the inner clearance diameter of the tubular shaft 12. The actuator element 26 can be pushed back and forth in the shaft by displacing the moveable gripping portion 22.

It is also possible that the moveable gripping portion 22 be fixed to the shaft 12 and the non-moveable gripping element 24 be fixed to the actuator element 26 through a slot in the shaft 12. In this case, the shaft 12 is shifted. These kinematic variations will be selected depending on whether the maximal force to be applied by the operator in simplest form is to be exerted for opening or for closing the working elements 14, 15. This is most easily provided for the operator in that the gripping portions 22, 24 are gripped by hand and the gripping portions 22, 24 are moved toward one another. The closing force plays a predominant role for grasping forceps and scissors, while the opening force is important for spreader or expander tools.

The distal end of the actuator element 26 is connected with the working elements 14, 15 through pivot joints to be described in more detail below. The pivot axes 38, 39 can be seen in FIG. 1, about which the working elements 14, 15 are rotated when the actuator element 26 is moved back and forth. In the condition illustrated in FIG. 1, the working elements 14, 15 are opened or spread apart.

The surgical instrument 10 is configured such that a further tube-like instrument 30 can be introduced into its proximal end. In the illustrated embodiment, an endoscope 32 can be introduced.

The outer diameter of the shaft 34 of the endoscope 32 corresponds approximately to the inner clearance diameter of the tube 28, which represents the actuator element 26. As illustrated in FIG. 1, the shaft 34 of the endoscope 32 is inserted through the instrument 10 to the extent that its distal end almost reaches the outer distal ends of the working elements 14, 15. This position can be employed when the surgical instrument 10 or its working elements 14, 15 are to be brought to a specific location. This can be visually monitored through the eyepiece 36 of the endoscope 32. If tissue is to be grasped and cut between the scissor-like jaws 16, 17, the endoscope 32 is withdrawn by a corresponding distance.

In the illustrated embodiment, an endoscope is inserted as a further instrument 30 of the surgical instrument 10. It will be understood that other correspondingly configured instruments may also be employed.

Figure 2:
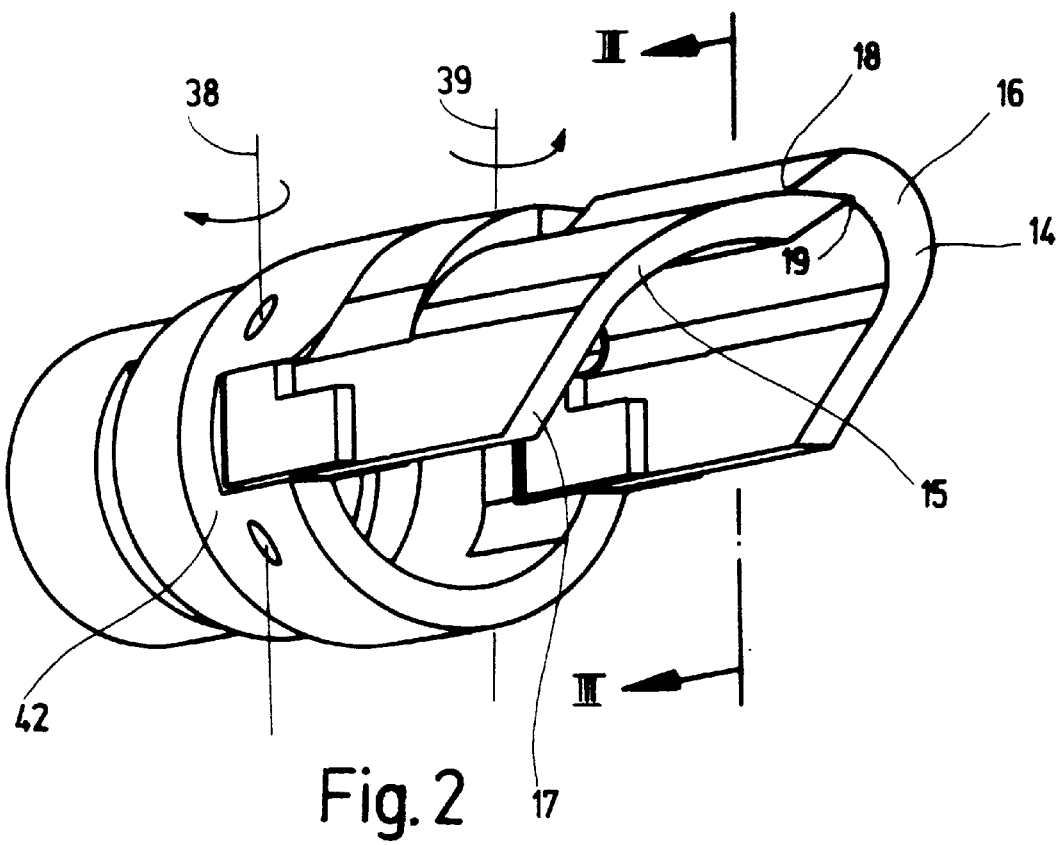
FIG. 2 shows a perspective view of the distal end of the surgical instrument.

The configuration of the working elements 14, 15 as scissorlike jaws 16, 17 and their controlled operation will now be described in more detail in conjunction with FIGS. 2 to 6. In FIG. 2, a tubular piece 42 is illustrated upon which the jaws 16, 17 are mounted. The tubular piece 42 is then inserted into the shaft 12 from its distal end and is secured thereto as can be seen in the cross-section of FIG. 4. This simplifies the manufacture and assembly of these components.

Figure 3:
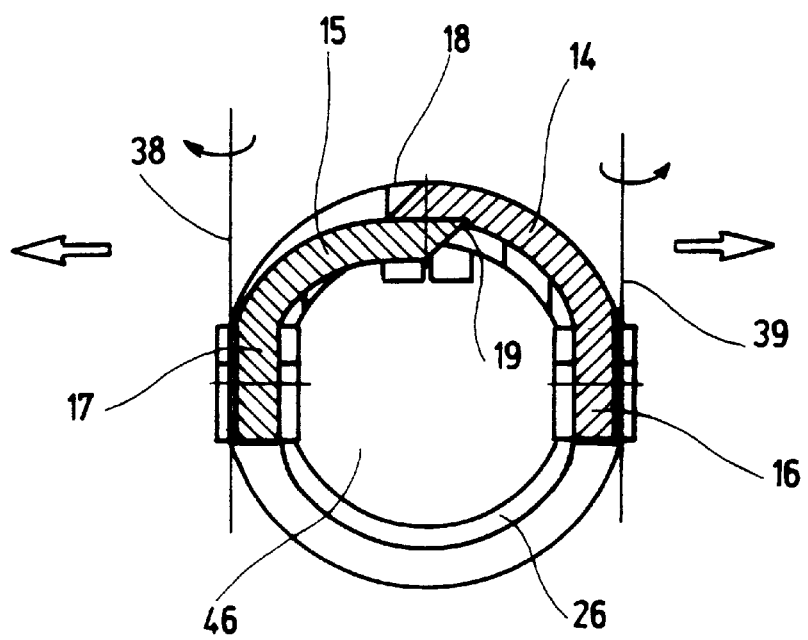
FIG. 3 shows a cross section along the line III—III in FIG. 2 or FIG. 4.
Figure 4:
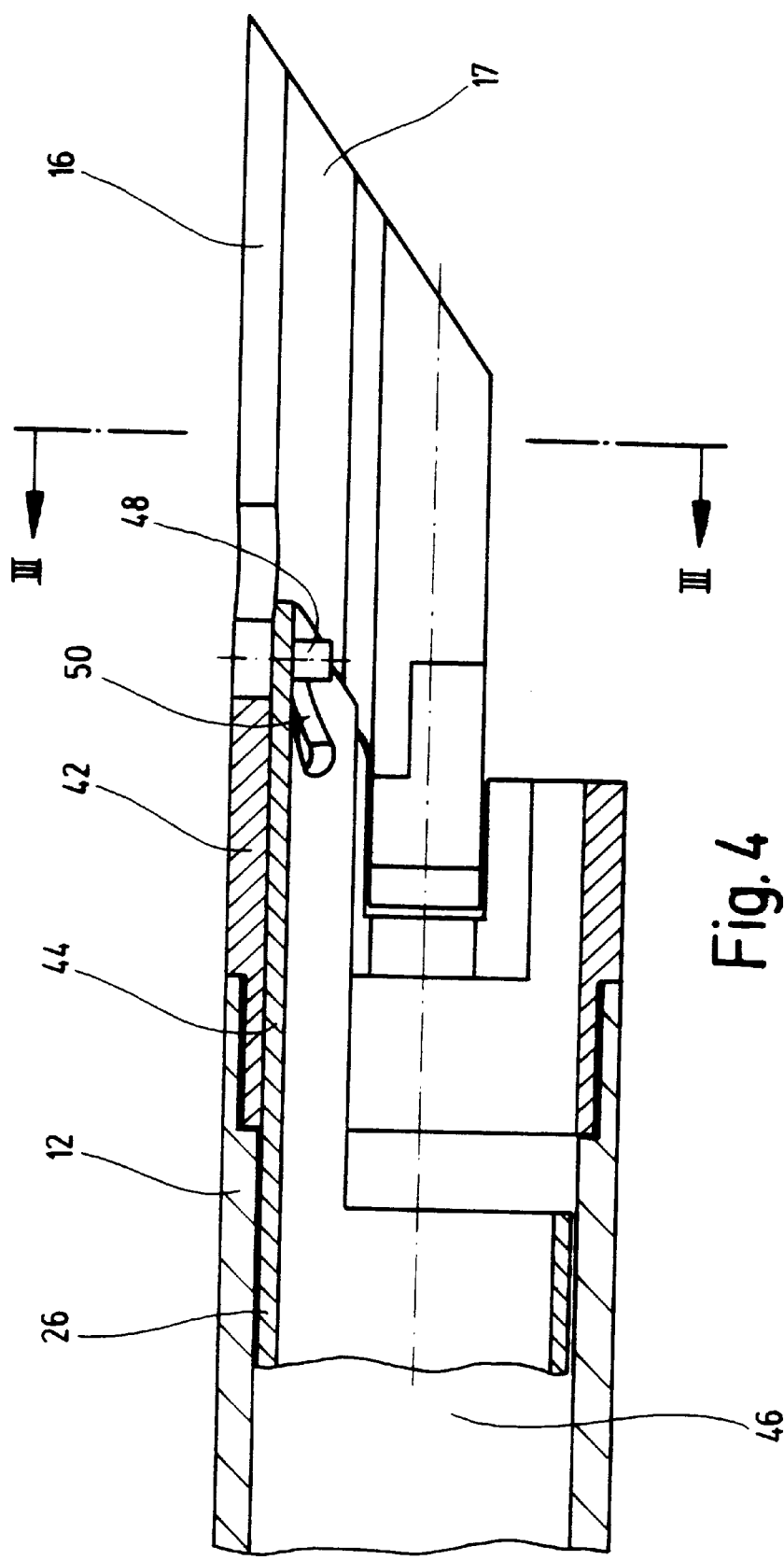
FIG. 4 shows a side view in partial cross section of the distal end region of the surgical instrument of FIG. 1.

As can be taken from FIGS. 2 and 3, the jaws 16, 17 are formed as sectional tube-like parts, which are connected to the tubular piece 42 by pivot pins (not shown) extending transversely to the longitudinal axis of the shaft 12. The center axes of these pivot pins are then the pivot axes 38, 39 of the jaws 16, 17.

The opposing edges 18, 19 of the jaws 16, 17 are configured such that they pass by one another in scissor-like manner, whereby a traumatically exact cut can be carried out. For this purpose, the edges 18, 19 are beveled, as best seen in the illustration of FIG. 3.

The jaw 16 represents a tubular section extending more than 90° in circumferential direction, which continues approximately as an extension of the tubular wall of the shaft 12. The other jaw 17 is bent radially inwardly in the region of its edge, so that it can be moved under the other jaw, i.e. radially further to the inside. In the spreading movement, the jaws 16, 17 separate from one another as illustrated by the arrows in FIG. 3. With movement in the opposite direction, they return to the closed position as illustrated in FIGS. 2 and 3. During this movement, the edges 18, 19 pass by one another in scissor-like manner.

Figure 5:
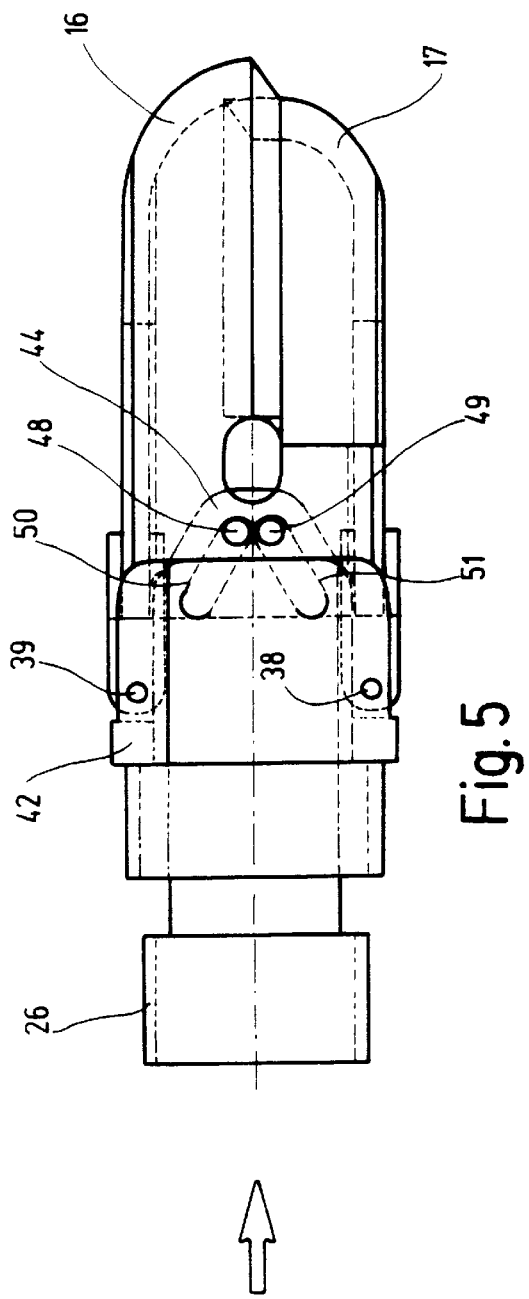
FIG. 5 shows a plan view of the distal end, rotated by 90° about the shaft axis compared to FIG. 4, where the jaw portions are closed.
Figure 6:
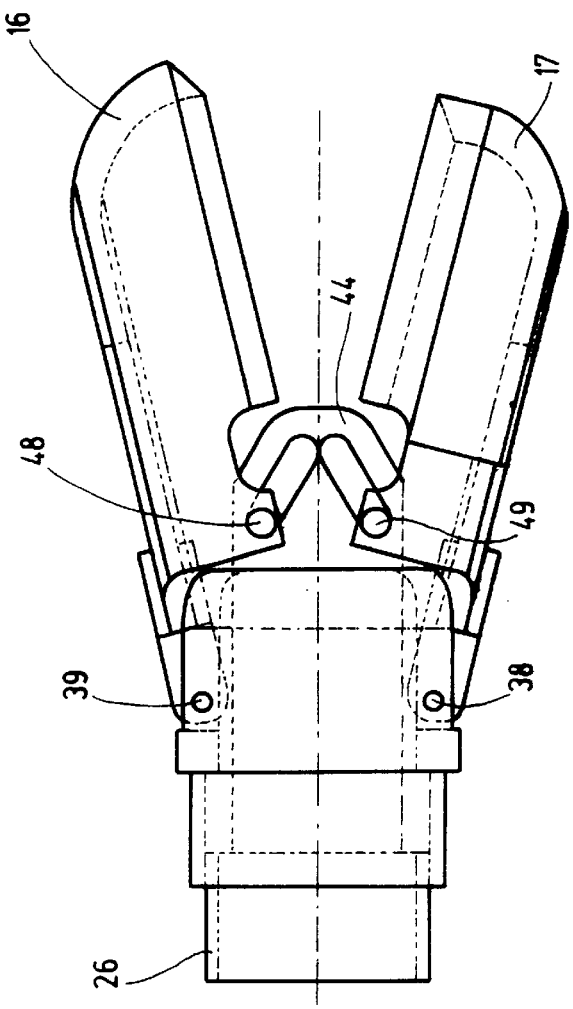
FIG. 6 shows an illustration comparable to FIG. 5 with the jaw portions being opened or spread apart.

The control of the spreading movement is best seen in FIGS. 5 and 6. Recesses acting as guide slots 50, 51 are provided on a distal projection 44 of the tube 28 of the actuator element 26. Guide pins 48, 49 engage in the slots, which project radially inwardly from the inside of the jaws 16, 17. The guide slots 50, 51 are formed as elongated holes, which approach one another in V-shape manner towards the distal end.

When the actuator element 26 starting from the closed position of the jaws 16, 17 as shown in FIG. 5 is pushed in distal direction as indicated by the arrows, the control pins 48, 49 are moved radially outwardly by the guide slots 50, 51. Consequently, the jaws 16, 17 are spread apart by pivoting about the axes 38, 39. When the actuator element 26 is moved in the proximal direction, the opposite procedure takes place, i.e. the jaws 16, 17 are closed.

This linear movement is achieved by the moveable gripping portion 22, which is in engagement with the actuator element 26. The kinematic reversed arrangement is possible, i.e. the moveable gripping portion is connected to the shaft and the non-moveable portion with the actuator element.

As best seen in FIG. 3, this construction allows a relatively larger inner hollow channel 46, which is not obstructed by bulky components and is not restricted by the opening and closing of the jaws, because the control mechanism and pivot joints are disposed in the periphery region. Thus a further instrument 30 can be inserted into the surgical instrument 10, which has only a slightly smaller outer diameter.

On the whole, the assembly of the surgical instrument 10 and the inserted further instrument 30 requires an extremely reduced radial dimension, as can be seen in FIG. 1. Thus both instruments can be inserted into the body or removed therefrom through a single small incision or a corresponding trocar.

What is claimed is:

1. A surgical instrument comprising
   a hollow tubular shaft
   working elements arranged at a distal end of said hollow tubular shaft,
   at least one of said working elements being spreadable apart,
   a handle arranged at a proximal end of said hollow tubular shaft an actuator element through which actuator element said working elements engage with said handle for opening and closing said working elements, and
   a continuous hollow channel provided within said shaft into which continuous hollow channel a further instrument may be introduced, said continuous hollow channel having a cross section corresponding approximately to an inner clearance diameter of said hollow tubular shaft,
   wherein said working elements are configured such that they do not extend into a cross section of an imaginary distal prolongation of said hollow channel either in opened or in closed position of said working elements, and
   wherein said working elements are configured as jaws of grasping forceps.

2. Surgical instrument of claim 1, wherein said working elements extend in said closed position as an extension of a tube wall of said hollow tubular shaft.

3. Surgical instrument of claim 1, wherein said working elements themselves are formed as tube sections.

4. Surgical instrument of claim 1, wherein said actuator element being tubular.

5. Surgical instrument of claim 1, wherein said actuator element having recesses acting as guide slots, into which guide slots guide pins of said working elements engage.

6. Surgical instrument of claim 1, wherein said actuator element engages with said working elements through pivotal intermediate means.

7. Surgical instrument of claim 1, wherein said actuator element engages said working elements through flexible intermediate means.

8. Surgical instrument of claim 1, wherein said working elements are mounted on said hollow tubular shaft through pivotal joints.

9. Surgical instrument of claim 1, wherein said working elements are mounted on said hollow tubular shaft through flexible joints.

10. Surgical instrument of claim 1, wherein said working elements being connected to said hollow tubular shaft via mounting points, said mounting points of said working elements being spaced as far as possible from one another in a circumferential direction.

11. Surgical instrument of claim 1, wherein said working elements being connected to said hollow tubular shaft via mounting points, said mounting points of said working elements being spaced as far as possible from one another in a circumferential direction.

12. Surgical instrument of claim 1, wherein said working elements are configured as jaws, said jaws are formed as adjacent tube section extending slightly over 90° in a circumferential direction, opposing edges of said adjacent tube section pass by one another in a scissor-like manner.

13. A surgical instrument comprising
   a hollow tubular shaft
   working elements arranged at a distal end of said hollow tubular shaft,
   at least one of said working elements being spreadable apart,
   a handle arranged at a proximal end of said hollow tubular shaft
   an actuator element through which said working elements engage with said handle for opening and closing said working elements, and
   a continuous hollow channel provided within said shaft into which continuous hollow channel a further instrument may be introduced, said continuous hollow channel having a cross section corresponding approximately to an inner clearance diameter of said hollow tubular shaft,
   wherein said working elements are configured such that they do not extend into a cross section of an imaginary distal prolongation of said hollow channel either in opened or in closed position of said working elements, and wherein said working elements are configured as jaws of a grasping forceps.

14. Surgical instrument of claim 13, wherein said working elements extend in said closed position as an extension of a tube wall of said hollow tubular shaft.

15. Surgical instrument of claim 13, wherein said working elements themselves are formed as tube sections.

16. Surgical instrument of claim 13, wherein said actuator element being tubular.

17. Surgical instrument of claim 13, wherein said actuator element having recesses acting as guide slots, into which guide slots guide pins of said working elements engage.

18. Surgical instrument of claim 13, wherein said actuator element engages with said working elements through pivotal intermediate means.

19. Surgical instrument of claim 13, wherein said actuator element engages said working elements through flexible intermediate means.

20. Surgical instrument of claim 13, wherein said working elements are mounted on said hollow tubular shaft through pivotal joints.

21. Surgical instrument of claim 13, wherein said working elements are mounted on said hollow tubular shaft through flexible joints.

22. Surgical instrument of claim 13, wherein said working elements are configured as jaws, said jaws are formed as adjacent tube section extending slightly over 90° in a circumferential direction, opposing edges of said adjacent tube section pass by one another in a scissor-like manner.

* * * * *